US008241245B2

(12) United States Patent
Markel et al.

(10) Patent No.: US 8,241,245 B2
(45) Date of Patent: Aug. 14, 2012

(54) CO-AXIAL CATHETER

(75) Inventors: David F. Markel, Collegeville, PA (US);
Earl W. Voorhees, Jr., Warrington, PA (US); Anthony J. Madison, Lansdale, PA (US); Timothy Schweikert, Levittown, PA (US); Mahase Nardeo, Collegeville, PA (US); Mark Fisher, Sellersville, PA (US)

(73) Assignee: Medical Components, Inc., Harleysville, PA (US)

( * ) Notice: Subject to any disclaimer, the term of this patent is extended or adjusted under 35 U.S.C. 154(b) by 1371 days.

(21) Appl. No.: 10/961,706

(22) Filed: Oct. 8, 2004

(65) Prior Publication Data
US 2005/0080398 A1 Apr. 14, 2005

Related U.S. Application Data

(60) Provisional application No. 60/509,626, filed on Oct. 8, 2003.

(51) Int. Cl.
*A61M 31/00* (2006.01)
*A61M 37/00* (2006.01)

(52) U.S. Cl. .................................................. 604/93.01
(58) Field of Classification Search .............. 604/43, 604/4.01, 5.01, 93.01, 533, 535, 48, 164.04, 604/264, 523, 44, 284, 263, 265–279, 524–532, 604/534, 536–539
See application file for complete search history.

(56) References Cited

U.S. PATENT DOCUMENTS

| 4,037,599 | A | * | 7/1977 | Raulerson ........................ 604/44 |
| 4,099,528 | A | | 7/1978 | Sorenson et al. |
| 4,202,332 | A | | 5/1980 | Tersteegen et al. |
| 4,270,535 | A | | 6/1981 | Bogue et al. |
| 4,493,696 | A | | 1/1985 | Uldall |
| 4,690,673 | A | | 9/1987 | Bloomquist |
| 5,053,004 | A | * | 10/1991 | Markel et al. ................... 604/43 |
| 5,207,648 | A | | 5/1993 | Gross |

(Continued)

FOREIGN PATENT DOCUMENTS
EP 0000041 A1 12/1978
(Continued)

OTHER PUBLICATIONS

International Search Report dated Apr. 19, 2006 from PCT/US04/33242 (3 pages).

(Continued)

*Primary Examiner* — Christopher D Koharski
*Assistant Examiner* — Pritesh Patel
(74) *Attorney, Agent, or Firm* — Glenn M. Massina, Esq.; Fox Rothschild LLP

(57) ABSTRACT

A co-axial catheter assembly including a first lumen having a first distal end and a first proximal end, and a second lumen having a second distal end and a second proximal end. The second lumen extends co-axially with the first lumen, wherein the second lumen is at least partially disposed within the first lumen and the second distal end extends distally of the first distal end. A catheter hub provides for fluid connections of the inner and outer lumens with respective extension tubes, and includes spacers that maintain the proximal end of the inner lumen concentrically within the proximal end of the outer lumen and the distal end of the inner lumen concentrically within the distal end of the outer lumen, respectively. Methods of manufacturing and of inserting the catheter are also disclosed.

11 Claims, 19 Drawing Sheets

U.S. PATENT DOCUMENTS

| | | | |
|---|---|---|---|
| 5,395,316 | A | 3/1995 | Martin |
| 5,409,455 | A | 4/1995 | Belden |
| 5,480,380 | A | 1/1996 | Martin |
| 5,718,678 | A | 2/1998 | Fleming, III |
| 5,718,692 | A | 2/1998 | Schon et al. |
| 5,792,105 | A | 8/1998 | Lin et al. |
| 5,947,953 | A | 9/1999 | Ash et al. |
| 5,961,485 | A | 10/1999 | Martin |
| 5,976,103 | A | 11/1999 | Martin |
| 6,942,635 | B2 * | 9/2005 | Rosenblatt et al. .......... 604/6.13 |
| 7,223,254 | B2 | 5/2007 | Hjalmarsson |
| 2002/0107506 | A1 | 8/2002 | McGuckin, Jr. et al. |

FOREIGN PATENT DOCUMENTS

| | | |
|---|---|---|
| EP | 0535874 A1 | 4/1993 |
| EP | 0 713 406 B1 | 3/1998 |
| JP | 6327774 A | 11/1994 |
| WO | WO 97/35629 A | 10/1997 |
| WO | WO 97/37699 | 10/1997 |
| WO | 99/44666 | 9/1999 |
| WO | WO 99/44666 A | 9/1999 |
| WO | WO 03/084596 A | 10/2003 |

OTHER PUBLICATIONS

Written Opinion dated Apr. 19, 2006 from PCT/US04/33242 (3 pages).

Supplementary European Search Report, EP 04794558, dated Aug. 23, 2007; (3 pages).

Theron, J., Courtheoux, P., Alachkar, F., Bouvard, G., Maiza, D.; "New Triple Coaxial Catheter System for Carotid Angioplasty with Cerebral Protection"; AJNR 11, Sep./Oct. 1990; pp. 869-874, American Society of Neuroradiology, Orlando, FL.

Office Action, Japanese Application No. 2006-534379 dated Nov. 10, 2009 (3 pages); translation (4 pages).

Office Action dated Dec. 29, 2009, Canadian Patent Application No. 2,541,789 (3 pages).

Office Action dated Jul. 8, 2010; Japanese Application No. 2006-534379 (6 pages).

Office Action dated Oct. 5, 2010; Canadian Application No. 2,541,789 (4 pages).

Office Action dated Apr. 5, 2011; Japanese Patent Application No. 2006-534379 (3 pages; English translation 2 pages).

* cited by examiner

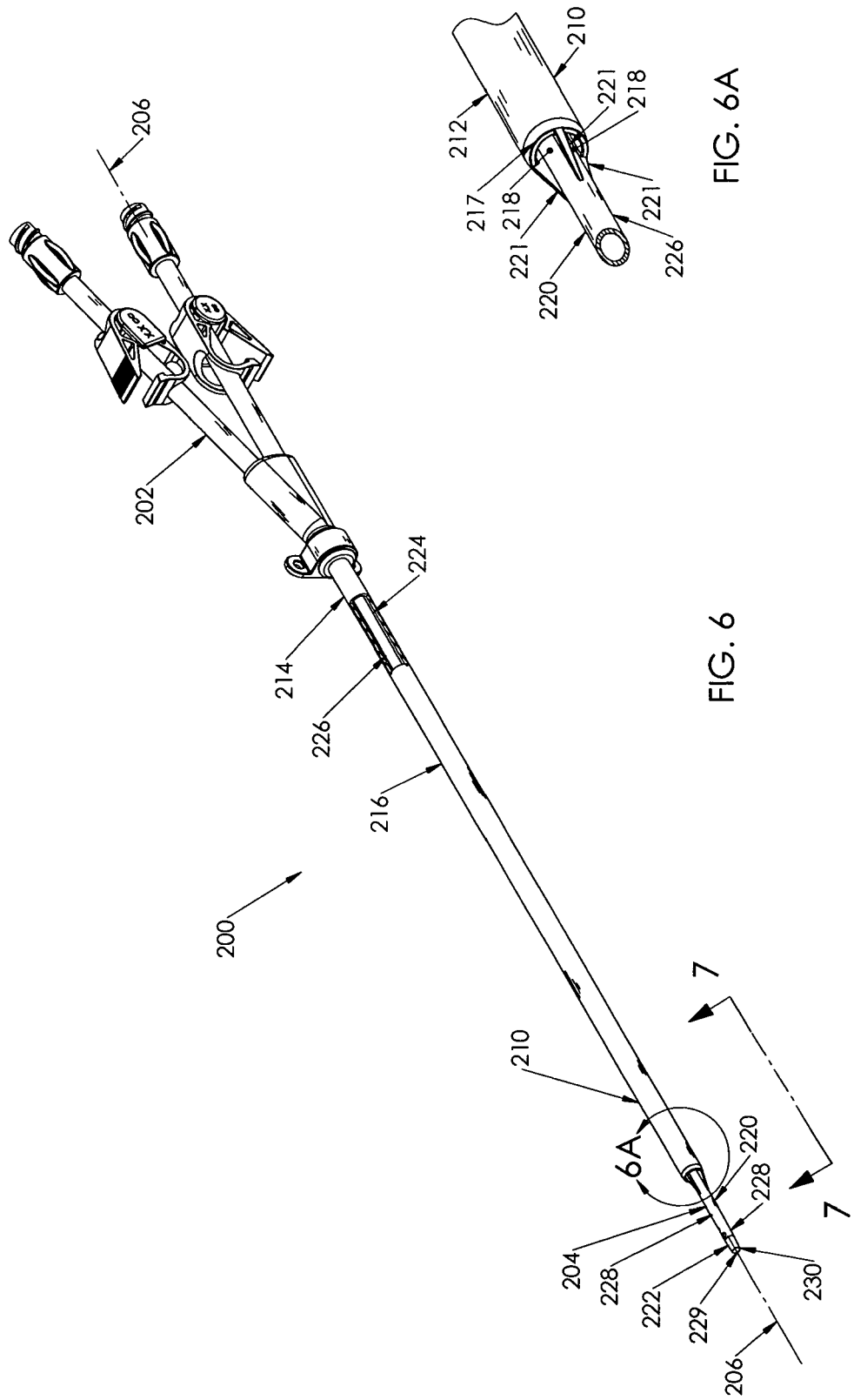

CO-AXIAL CATHETER

CROSS-REFERENCE TO RELATED APPLICATION

The application claims the benefit of U.S. Provisional Patent Application Ser. No. 60/509,626, filed on 8 Oct. 2003.

BACKGROUND OF THE INVENTION

Catheters for the introduction or removal of fluids may be located in various venous locations and cavities throughout the body for introduction or removal of these fluids. Such catheterization may be performed by using a single catheter having multiple lumens. A typical example of a multiple lumen catheter is a dual lumen catheter in which one lumen introduces fluid and the other lumen removes fluid. An example of such multiple lumen catheter is the SPLIT-CATH® catheter.

Generally, to insert any catheter into a blood vessel, the vessel is identified by aspiration with a long hollow needle in accordance with the well known Seldinger technique. When blood enters a syringe attached to the needle, indicating that the vessel has been found, a thin guide wire is then introduced, typically through a syringe needle or other introducer device into the interior of the vessel. The introducer device is then removed, leaving the guide wire within the vessel. The guide wire projects beyond the surface of the skin. At this point, several options are available to a physician for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire, for example, for insertion of small diameter dual lumen catheters. If the catheter to be inserted is significantly larger than the guide wire, a dilator device is passed over the guide wire to enlarge the hole. The catheter is then passed over the guide wire, and the guide wire and dilator are then removed.

Several different designs of dual lumen catheters are known. One design incorporates side-by-side lumens in which one lumen (the arterial lumen) draws fluid from the body and the other lumen (the venous lumen) delivers fluid to the body. The venous lumen is typically longer than the arterial lumen to reduce recirculation of the fluid. One drawback of the side-by-side catheter is the fact that, during use, the suction effect of the arterial lumen occasionally draws the side wall of the vessel into which the catheter is, inserted against the lumen, effectively reducing the ability of fluid to flow into the catheter.

An alternative design is a coaxial design, such as is disclosed in U.S. Pat. No. 5,480,380. In such a catheter design, the arterial lumen is peripheral to the venous lumen, which extends along the longitudinal axis of the catheter. Like the side-by-side catheter, the venous lumen in the coaxial catheter is typically longer than the arterial lumen to reduce recirculation. One problem with this design is that the inlet openings on the arterial lumen are on the sides of the lumen. The most proximal opening is typically the only opening that receives heparin or other anti-clotting agent in between treatments, allowing the remaining openings to clot. Also, the suction effect of the arterial lumen may draw the lumen against the side wall of the vessel, reducing the available surface area of the openings, thereby restricting flow into the lumen.

It would be beneficial to provide a coaxial catheter that reduces the potential for a suction effect of the arterial lumen against a vessel wall, and maximizes the amount of fluid that may be taken in by the lumen during catheter operation.

BRIEF SUMMARY OF THE PRESENT INVENTION

Briefly, the present invention provides a co-axial catheter comprising a first lumen extending along an axis and a second lumen extending along the axis. The first lumen has an open first distal end and a first proximal end and the second lumen is disposed generally within the first lumen. The second lumen also includes a second distal end extending distally of the first distal end. At least one spacer is disposed between the first lumen and the second lumen at the distal end of the first lumen.

Further, the present invention also provides a co-axial catheter comprising a first lumen having a first distal end, a first proximal end, and a longitudinal axis extending therethrough and a second lumen having a second distal end, a second proximal end, and extending co-axially with the first lumen. The second lumen is at least partially disposed within the first lumen. The second distal end extends distally of the first distal end, wherein the second distal end includes a distal tip and a bulbous projection disposed between the distal tip and the first distal end.

Also, the present invention provides a method of inserting a catheter comprising providing a catheter having a first lumen having a first distal end, a first proximal end, and a longitudinal axis extending therethrough and a second lumen having a second distal end, a second proximal end, and extending co-axially with the first lumen. The second lumen is at least partially disposed within the first lumen and the second distal end extends distally of the first distal end. The second distal end includes a distal tip and a bulbous projection disposed between the distal tip and the first distal end. The method further comprises inserting the distal tip into a blood vessel; and oscillating the distal tip in a generally circular motion while advancing the distal tip into the vessel.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 6 is a perspective view, partially broken away, of a catheter assembly according to a second embodiment of the present invention.

FIG. 6A is an enlarged perspective view of the distal end of the outer lumen of the catheter assembly shown in FIG. 6.

DETAILED DESCRIPTION OF THE INVENTION

Figure 1:
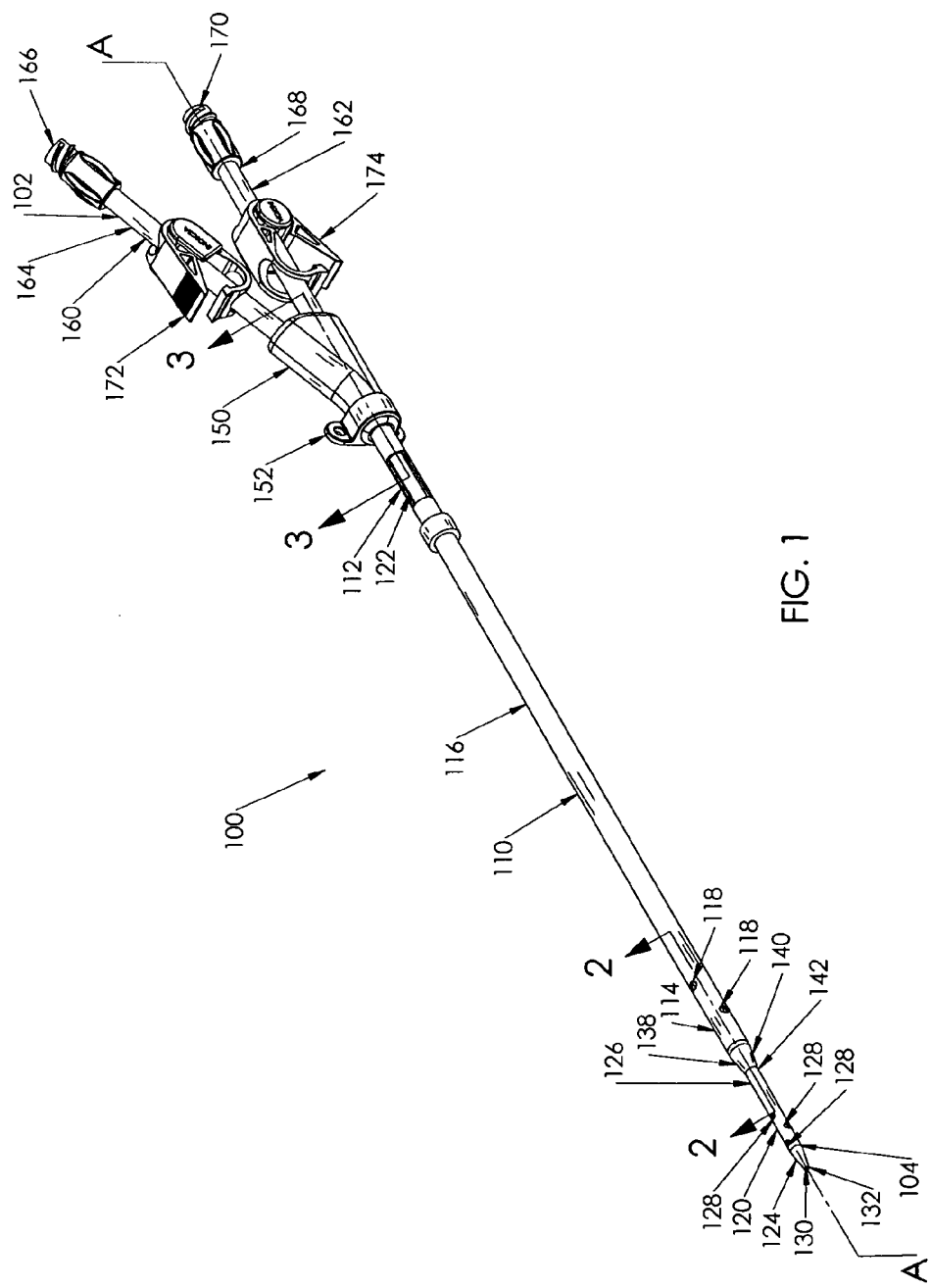
FIG. 1 is a perspective view of a catheter assembly according to a first embodiment of the present invention.

In the drawings, like numerals indicate like elements throughout. As used herein, the term "distal" is defined to mean a direction closer to the insertion end of the catheter and the term "proximal" is defined to mean a direction closer to the end of the catheter that remains exterior of the patient after insertion.

Figure 2:
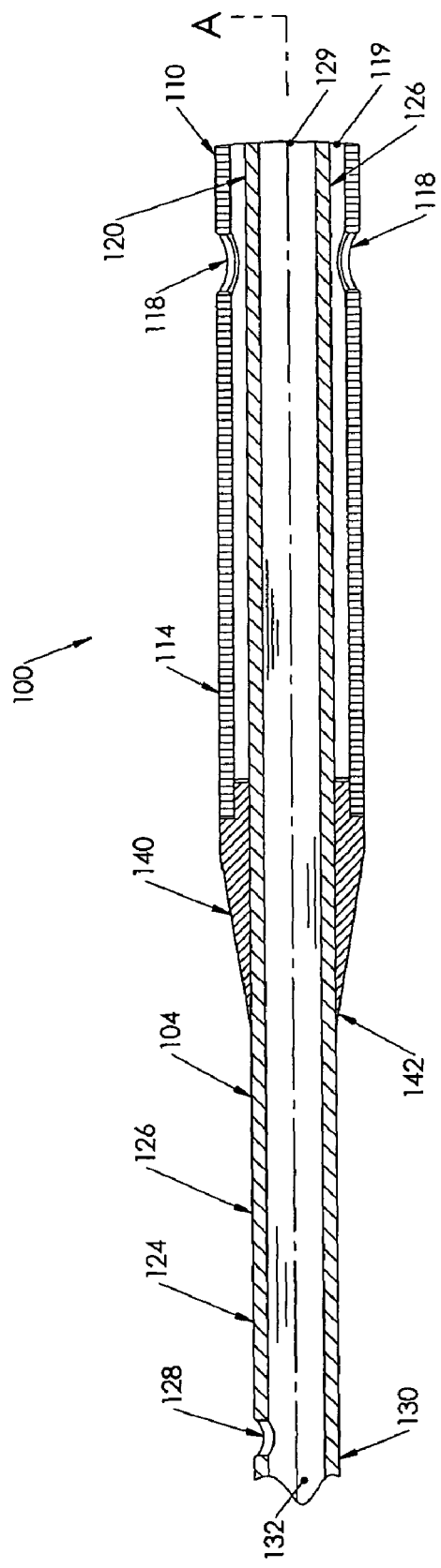
FIG. 2 is an enlarged side profile view, in section, of a distal end of the catheter assembly of FIG. 1.

A perspective view of a co-axial catheter assembly 100 according to a first embodiment of the present invention is shown in FIG. 1, with a partial sectional view shown in FIG. 2. The catheter assembly 100 includes a proximal end 102 and a distal end 104. The catheter assembly 100 also includes an outer lumen 110 and an inner lumen 120, with both the outer lumen 110 and the inner lumen 120 being co-axial along longitudinal axis "A". The outer lumen 110 includes a proximal end 112, a distal end 114, and a generally cylindrical body 116 extending between the proximal end 112 and the distal end 114. Preferably, the body 116 has an outer diameter of approximately 0.50 cm (0.19") and an inner diameter of approximately 0.38 cm (0.15").

The body 116 includes a plurality of side openings 118 helically spaced along the body 116 proximate to the distal end 114 of the outer lumen 110. Preferably, approximately five side openings 118 are present, although more or less than five side openings 118 may be used. Preferably, also, each side opening 118 has a diameter of approximately 0.17 cm (0.07"). Preferably, the outer lumen 110 is constructed from TECOFLEX® having a hardness of 85A on the Shore Durometer scale.

The inner lumen 120 includes a proximal end 122, a distal end 124, and a generally cylindrical body 126 extending between the proximal end 122 and the distal end 124. Preferably, the body 126 has an outer diameter of approximately 0.28 cm (0.11") and an inner diameter of approximately 0.23 cm (0.09"). Since the outer diameter of the inner lumen body 126 is smaller than the inner diameter of the outer lumen body 116, a first passageway 119 (see FIG. 2) is formed between the outer lumen body 116 and the inner lumen body 126. Also, since the outer lumen body 116 and the inner lumen body 126 are co-axial along the longitudinal axis "A", the first passageway 119 has a generally annularly shaped cross section. The first passageway 119 fluidly communicates with each of the openings 118 and serves to draw fluid, such as blood, from the body of the patient into which the catheter assembly 100 has been inserted.

The distal end 124 of the inner lumen 120 extends distally of the distal end 114 of the outer lumen 110. The body 126 includes a plurality of side openings 128 helically spaced along the body 126 proximate to the distal end 124 of the inner lumen 120. Preferably, approximately five side openings 128 are present, although more or less than five side openings 128 may be used. Preferably, also, each side opening 128 has a diameter of approximately 0.10 cm (0.04"). A second passageway 129 is formed in the inner lumen 120, and serves to return the fluid that was drawn from the patient's body by the first passageway 119 and/or add additional fluids, such as medicaments, into the patient.

A distal tip 130, located at the distal most end of the distal end 124, includes a conical taper and an opening 132 located along the longitudinal axis "A". Preferably, the opening 132 has a diameter of approximately 0.10 cm (0.04"). Preferably, the inner lumen 120 is constructed from TECOFLEX® having a hardness of 60D on the Shore Durometer scale.

While the outer lumen and inner lumen 110, 120, respectively, are preferably constructed from TECOFLEX®, those skilled in the art will recognize that the lumens 110, 120 may alternatively be constructed from another biocompatible plastic or elastomer, more preferably from a biocompatible elastomer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the lumens 110, 120, it is most preferred that the polymeric material includes a polyurethane or a polyolefin polymeric material having a preferably soft durometer, as specified below.

Suitable, preferred, biocompatible elastomers for use in forming the lumens 110, 120 include biocompatible elastomers such as medical grade silicone rubbers, polyvinyl chloride elasfomers, polyolefin homopolymeric and copolymeric elastomers, urethane-based elastomers, and natural rubber or other synthetic rubbers. Preferably, the lumens 110, 120 are made of the elastomeric material such that they are flexible, durable, soft, and easily conformable to the shape of the area to be catheterized and minimize risk of harm to vessel walls. If the lumens 110, 120 are used for hemodialysis applications, they are preferably formed of a soft silicone elastomer which has a hardness of at least about 60-D on a Shore durometer scale. Such an elastomer is available from Dow Coming, and can include 20% barium sulfate in the elastomer to provide radiopacity. While it is preferred to have a higher Shore durometer hardness if a biocompatible elastomer is used, particularly for hemodialysis, it is also possible to make a device from an elastomer having a lower Shore durometer hardness without departing from the spirit of the invention. It will be understood, based on this disclosure, that the lumens 110, 120 may also be radiopaque depending on their intended use.

A spacer 140 is disposed between the outer lumen 110 and the inner lumen 120 at the distal end 114 of the outer lumen 110. The spacer 140 closes off the distal end 114 of the outer lumen 110 and forms a tapered portion 142 extending distally from distal end 114 that fixedly connects the distal end 114 of the outer lumen 110 to the distal end 124 of the inner lumen 120. An enlarged sectional view of the distal end 124 of the catheter assembly 100, showing the spacer 140, is shown in FIG. 2.

Figure 3:
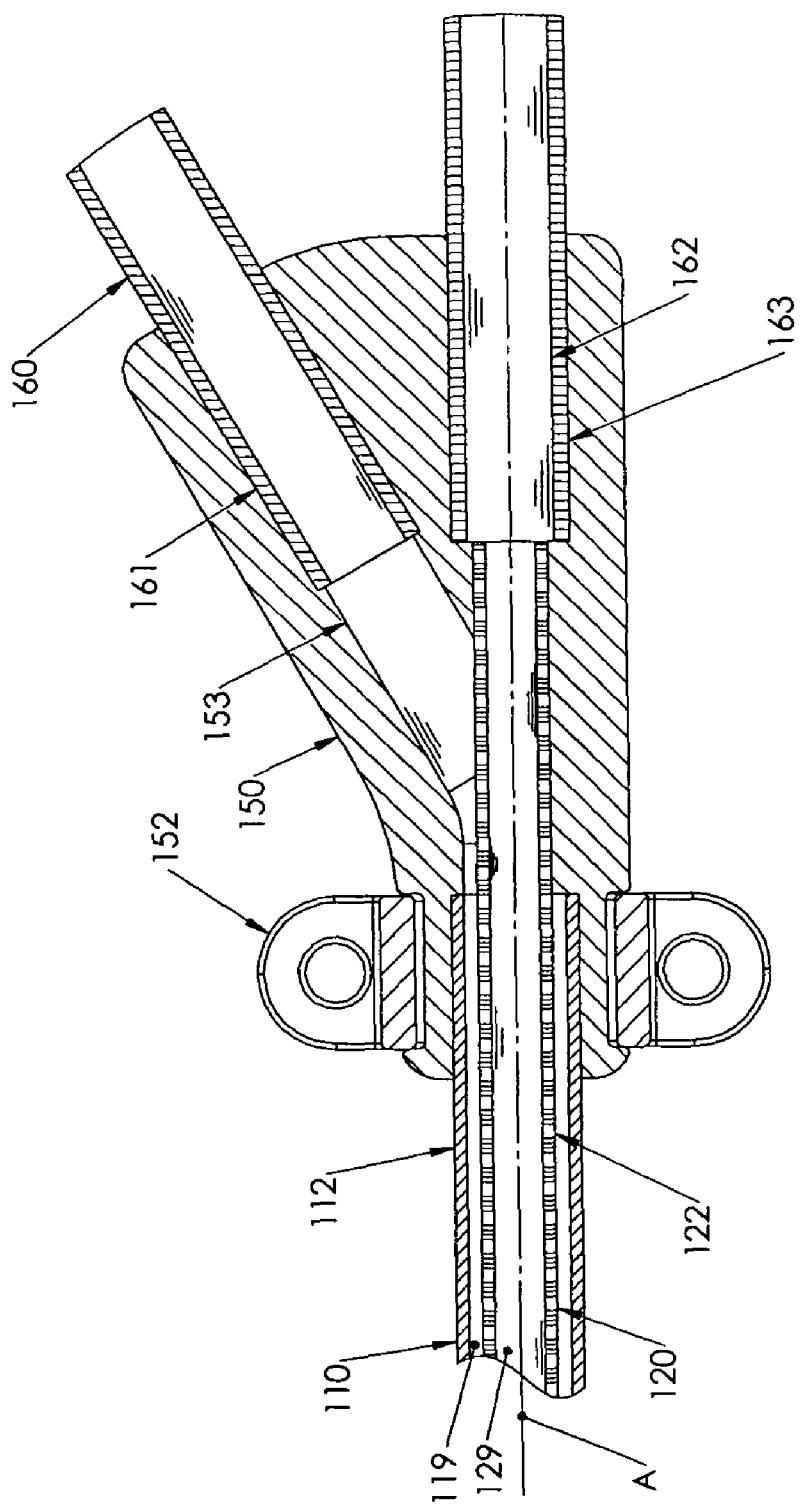
FIG. 3 is an enlarged perspective view, in section, of a hub portion of the catheter assembly of FIG. 1.

Referring now to FIG. 3, the proximal end 112 of the outer lumen 110 and the proximal end 122 of the inner lumen 120 both terminate in a hub 150. Inside the hub 150, the inner lumen 120 exits the outer lumen 110. Optionally, referring to FIG. 3A, a spacer 151 may be disposed between the proximal end 112 of the of the outer lumen 110 and the proximal end 122 of the inner lumen 120 to maintain the coaxial relationship of the inner lumen 120 with respect to the outer lumen 110. Preferably, the spacer 151 has a concave upper face that is curved to match the outer curvature of the inner lumen 120 and a convex lower face that is curved to match the inner curvature of the outer lumen 110.

Figure 3A:
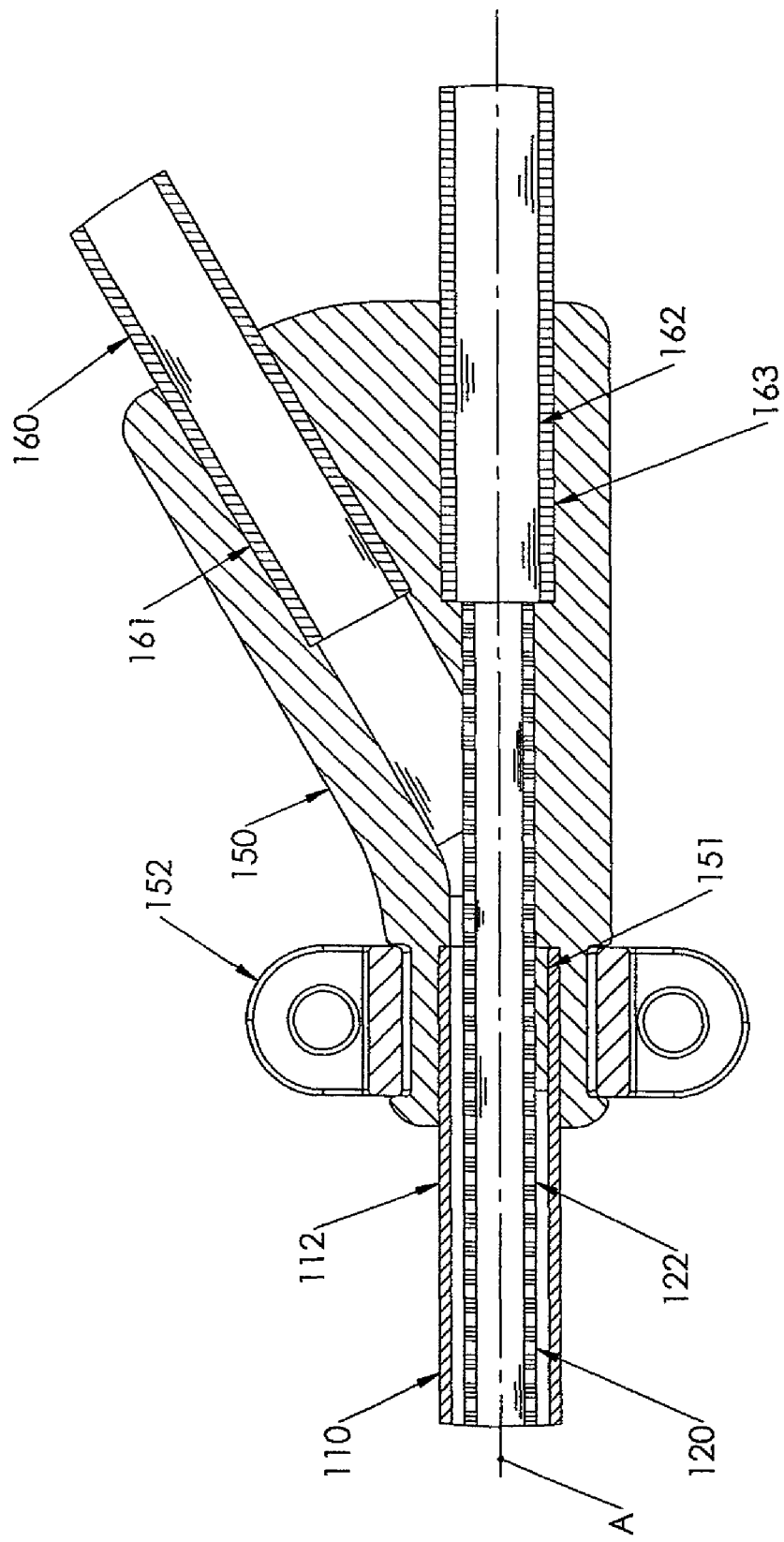
FIG. 3A is an enlarged side profile view, in section, of the hub portion of FIG. 3, with a first embodiment of a spacer inserted therein.
Figure 3B:
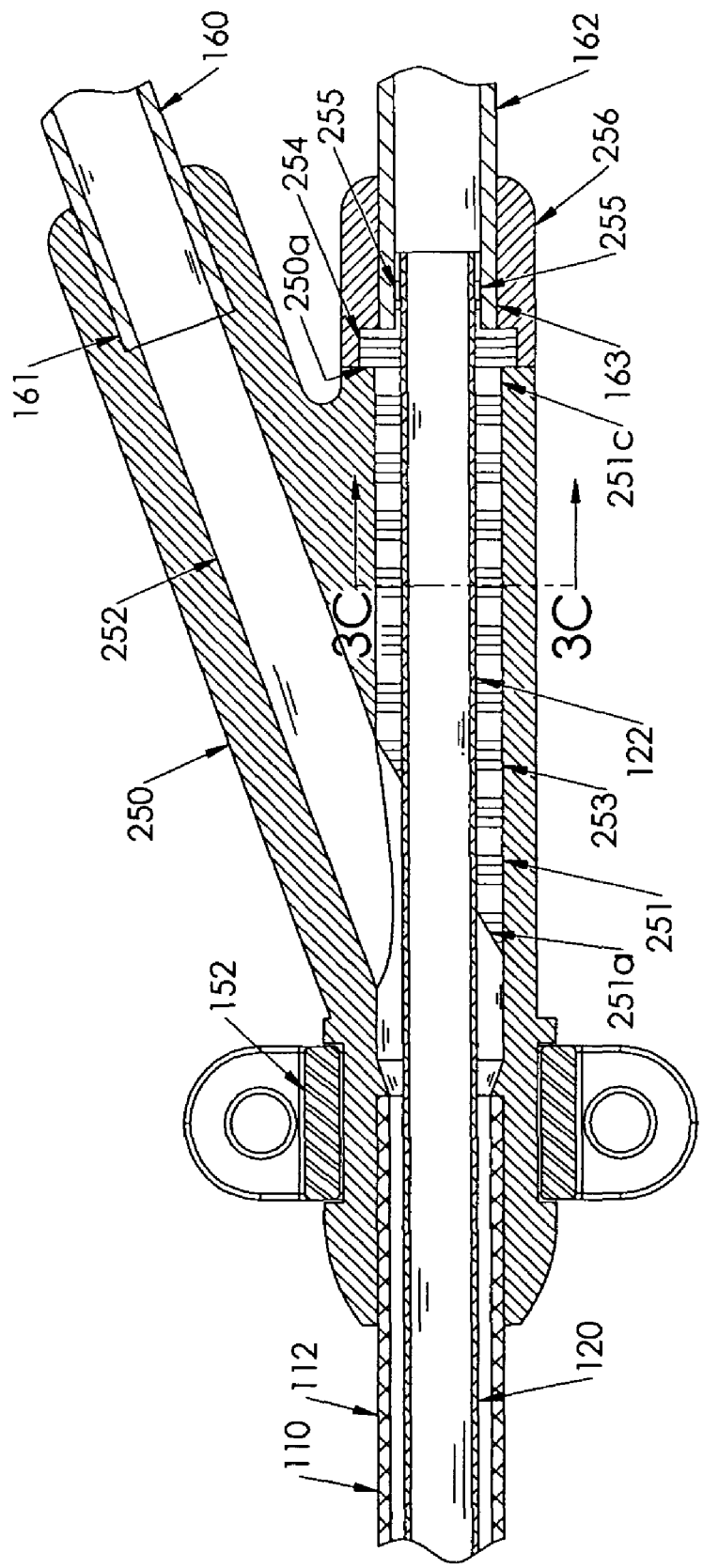
FIG. 3B is an enlarged side profile view, in section, of an alternate embodiment of a hub portion, with a second embodiment of a spacer inserted therein.

Alternatively, a hub 250 is shown in FIG. 3B. The hub 250 is similar to the hub 150 as described above, but the hub 250 includes a hub cap 256 at a proximal end 250a of the hub 250. In order to maintain spacing of the inner lumen 120 and the outer lumen 110, a spacer 251 may be inserted into the hub 250 proximally of the junction of venous and arterial hub passageways 252, 253, respectively. The spacer 251 preferably includes a beveled distal end 251a to block the venous passageway 253 and to direct fluid flow through the arterial passageway 252 between the outer lumen 110 and a first extension tube 160. The arterial passageway 252 tapers to a narrowed diameter at the proximal end 112 of the outer lumen 110 in order to provide enhanced fluid flow through the arterial passageway 252 and to provide a positive stop for the proximal end 112 of the outer lumen 110. As shown in the cross-sectional view of FIG. 3C, the spacer 251 also includes a key 251b that serves to properly align the spacer 251 within a keyway 253a in the venous passageway 253 and to properly align the tapered distal end 251a to properly block the venous passageway 253.

Referring back to FIG. 3B, a proximal end 251c of the spacer 251 includes a stepped member 254 that engages the proximal end 250a of the hub 250. The proximal end 251c of the spacer 251 also includes a plurality of through openings 255 located proximally of the stepped member 254. The through openings 255 allow a wicking adhesive, such as LOCTITE®, to be inserted therein to wick along the boundary between the inner lumen 120 and the spacer 251 to secure the spacer 251 to the inner lumen 120.

The hub cap 256 is disposed over the proximal end 250a of the hub 250 to sandwich the stepped member 254 between the proximal end 250a of the hub 250 and the hub cap 256. The hub cap 256 provides a connection point for a second extension tube 162 to enable fluid communication between the second extension tube 162 and the inner lumen 120.

Figure 3C:
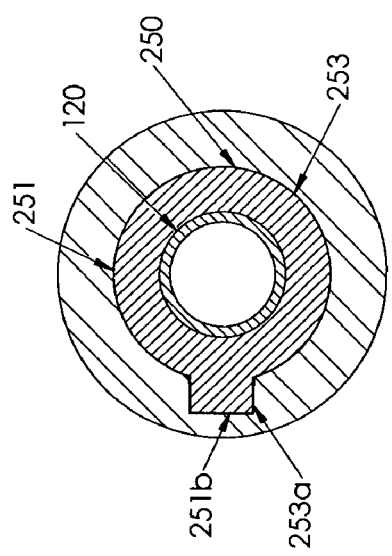
FIG. 3C is a sectional view of the hub portion and spacer taken along lines 3C-3C of FIG. 3B.
Figure 3D:
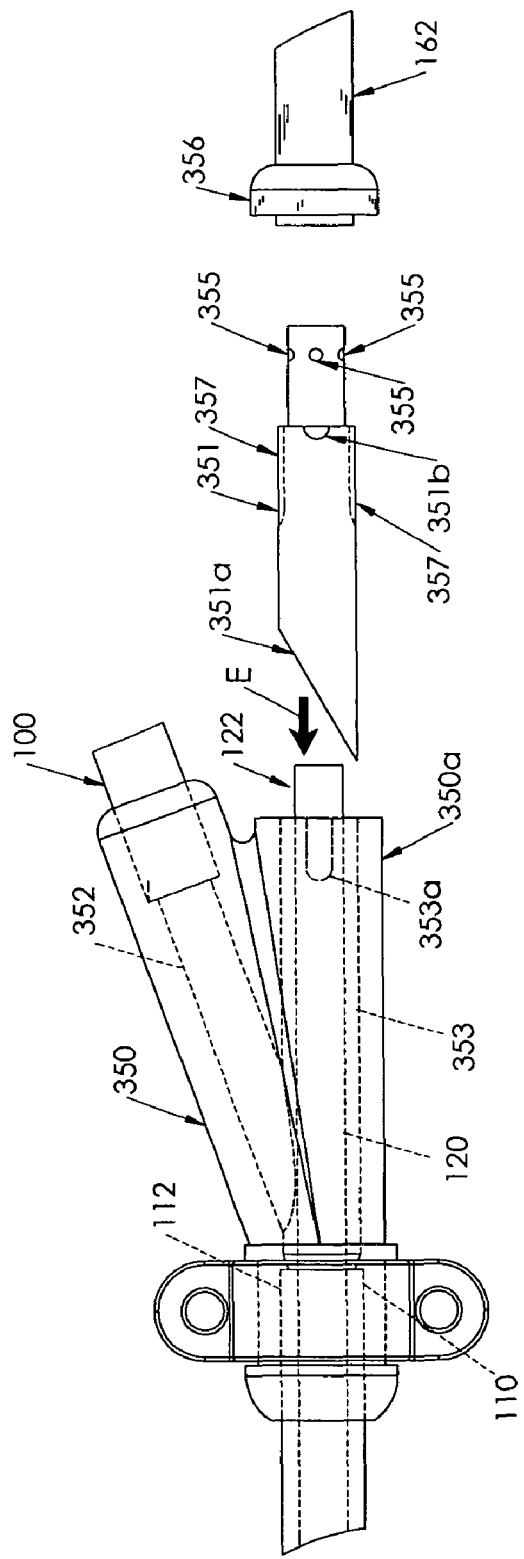
FIG. 3D is an enlarged side profile exploded cross-sectional view of a hub portion of another alternate embodiment of a hub portion, with a third embodiment of a spacer for being inserted therein.
Figure 3E:
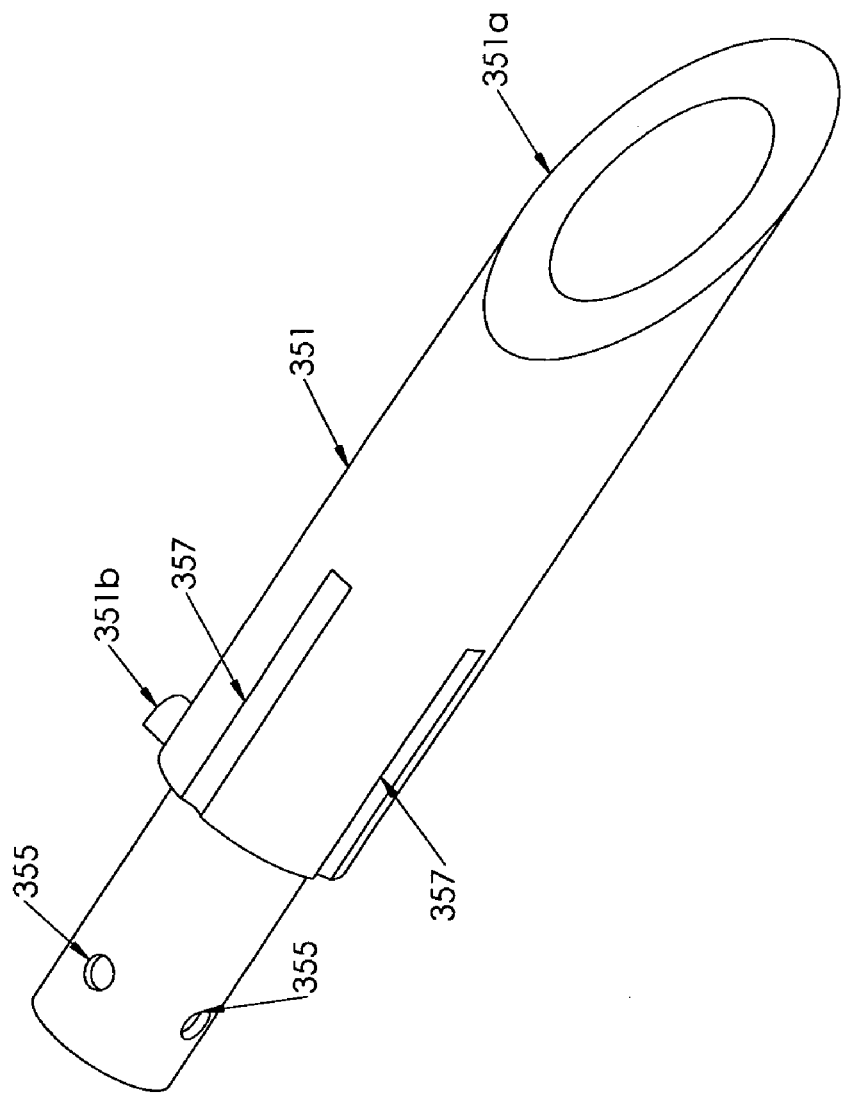
FIG. 3E is an enlarged perspective view of the third embodiment of the spacer shown in FIG. 3D.

Another embodiment of a hub 350 that may be used with the catheter assembly 100 is shown in FIGS. 3D and 3E. The hub 350 includes a spacer 351 that is disposed within the proximal end 350a of the hub 350. The spacer 351 is inserted over the proximal end 122 of the inner lumen 120 and into the hub 350 in the direction of the arrow E. The spacer 351 includes a plurality of through openings 355 located at the proximal end of the spacer 351. The through openings 355 allow a wicking adhesive, such as LOCTITE®, to be inserted therein to wick along the boundary between the inner lumen 120 and the spacer 351 to secure the spacer 351 to the inner lumen 120. The spacer 351 also include a plurality of longitudinal channels 357 that extend along the exterior of the spacer 351. The channels 357 allow an adhesive, such as LOCTITE®, to be inserted therein to wick along the boundary between the spacer 351 and the hub 350 to secure the spacer 351 within the hub 350. Although not shown, a transverse channel may be formed along the exterior of the spacer 351 at distal ends of the channels 357 to fluidly connect the channels 357 to each other, and to allow the adhesive to provide a circumferential seal between the hub 350 and the spacer 351.

The spacer 351 preferably includes a tapered distal end 351a to block the venous passageway 353 and to direct fluid flow through the arterial passageway 352 between the outer lumen 110 and the first extension tube 160. The arterial passageway 352 tapers to a narrowed diameter at the proximal end 112 of the outer lumen 110 in order to provide enhanced fluid flow through the arterial passageway 352 and to provide a positive stop for the proximal end 112 of the outer lumen 110. The spacer 351 also includes a key 351b that serves to properly align the spacer 351 within a keyway 353a in the venous passageway 353 and to properly align the tapered distal end 351a to properly block the venous passageway 353.

A hub cap 356 is overmolded proximate of the proximal end 350a of the hub 350 to fixedly retain the spacer 351 within the hub 350 and the hub cap 356. During overmold, some hub cap material may flow into the keyway 353a proximal of the key 350a to retain the spacer 351 within the hub 350. The hub cap 356 provides a connection point for a second extension tube 162 to enable fluid communication between the second extension tube 162 and the inner lumen 120.

While the remainder of the description of the hub portion of the catheter assembly 100 recites the hub 150 without the spacer 151, those skilled in the art will recognize that the same description applies to either the hub 150 with the spacer 151 or to either the hub 250 or the hub 350. Referring back to FIG. 3, the proximal end 112 of the outer lumen 110 fluidly communicates with a first extension tube 160 within the hub 150. A distal end 161 of the first extension tube 160 is disposed within and secured by the hub 150. The proximal end 122 of the inner lumen 120 fluidly communicates with a second extension tube 162 within the hub 150. A distal end 163 of the second extension tube 162 is disposed within and is secured by the hub 150. A passage 153 within the hub 150 between the proximal end 112 of the outer lumen 110 and the first extension tube 160 bends within the hub 150 at an angle of approximately 20 degrees away from the longitudinal axis "A", while the proximal end 122 of the inner lumen 120 and the second extension tube 162 both extend along the longitudinal axis "A". A suture wing 152 is disposed on the hub 150 to secure the hub 150 to the patient after insertion of the catheter assembly 100 into the patient.

Figure 4:
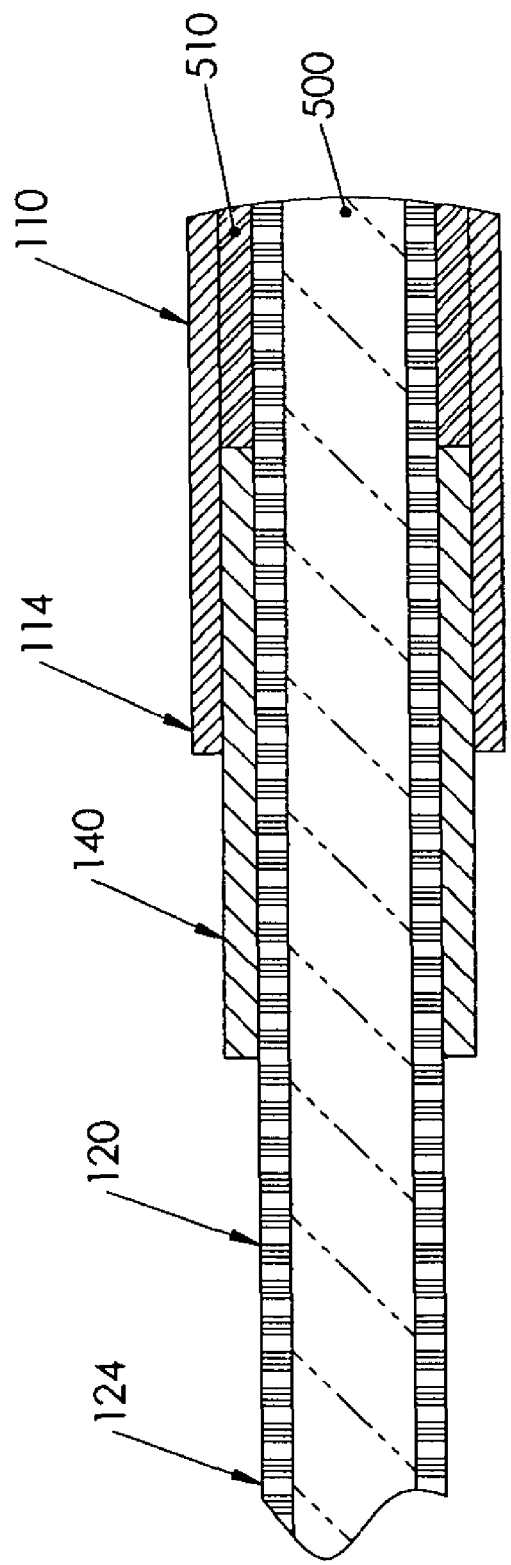
FIG. 4 is a sectional view showing the manufacturing of the distal end of the catheter assembly of FIG. 1.

Referring back to FIG. 1, a proximal end 164 of the first extension tube 160 terminates in a first luer lock 166, while a proximal end 168 of the second extension tube 162 terminates in a second luer lock 170. A first tube clamp 172 is disposed over the first extension tube 160 between the hub 150 and the first luer lock 166, while a second tube clamp 174 is disposed over the second extension tube 162 between the hub 150 and the second luer lock 168. To manufacture the catheter assembly 100, the inner lumen 120 and the outer lumen 110 are manufactured separately according to known methods, such as by extrusion. After manufacture, the inner lumen 120 is disposed over a first distal mandrel 500 as seen in FIG. 4. The first distal mandrel 500 is an elongated, preferably solid circular cylinder with an outer diameter slightly less than the inner diameter of the inner lumen 120 so that the inner lumen 120 is easily slid over the first distal mandrel 500.

A second distal mandrel 510 is partially disposed over the inner lumen 120 such that the distal end 124 of the inner lumen 120 extends distally beyond the second distal mandrel 510. The second distal mandrel 510 is an elongated, open ended hollow cylinder with an inner diameter slightly larger than the outer diameter of the inner lumen 120, and an outer diameter slightly less than the inner diameter of the outer lumen 110.

The outer lumen 110 is disposed over the second distal mandrel 510 such that the distal end 114 of the outer lumen 110 extends slightly distally of the second distal mandrel 510, but not as far distally as the distal end 124 of the inner lumen 120. Also, though not shown in FIG. 4, the proximal end 122 of the inner lumen 120 extends exterior of the proximal end 112 of the outer lumen 110. The spacer 140 is disposed over the distal end 124 of the inner lumen 120, and translated longitudinally along the inner lumen 120 until the spacer 140 engages the second distal mandrel 510. The distal ends 124, 114 of the inner lumen 120 and the outer lumen 110, as well as the spacer 140, are treated, such as by ultrasonic welding, to fuse the distal end 114 of the outer lumen 110 to the proximal and exterior portion of the spacer 140 and to fuse the inner portion of the spacer 140 to the inner lumen 120. The spacer 140 is also tapered during the fusing to a generally conical shape, providing a smooth transition between the outer diameter of the inner lumen 120 and the distal end 114 of the outer lumen 110. The distal tip 130 is also heat treated and shaped to form a tapered shape, as shown in FIG. 2.

Figure 5:
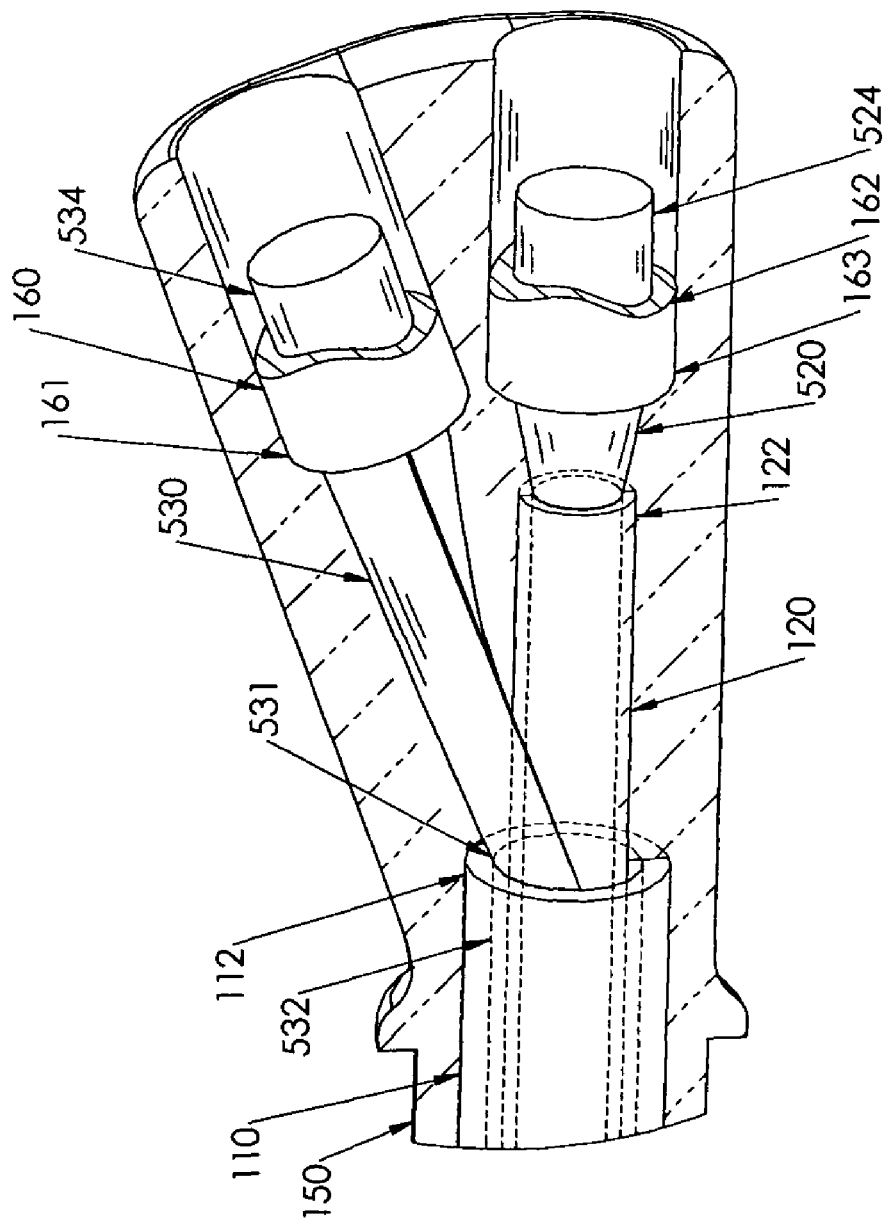
FIG. 5 is an enlarged perspective view, in partial section, showing the manufacturing of the hub portion of the catheter assembly of FIG. 1.

After the distal end 104 of the catheter assembly 100 is formed, the distal mandrels 500, 510 are removed, with the second distal mandrel 510 being removed from the proximal end 112 of the outer lumen 110. The distal tip 130 and the side openings 118, 128 are manufactured according to well-known methods. Next, as shown in FIG. 5, a first proximal mandrel 520 is inserted into the proximal end 122 of the inner lumen 120. The first proximal mandrel 520 is an elongated, preferably solid circular cylinder with an outer diameter slightly less than the inner diameter of the inner lumen 120 so that the inner lumen 120 is easily slid over the first proximal mandrel 520. A second proximal mandrel 530 is then slid into the proximal end 112 of the outer lumen 110, but exterior to the inner lumen 110. The second proximal mandrel 530 is an elongated, preferably solid piece with a bend 531 of approximately 20 degrees, with a distal portion 532 of the second proximal mandrel 530 extending approximately 3 cm distal of the bend 531. The distal portion 532 tapers from a generally cylindrical cross section to a generally U-shaped cross-section from the bend 531 to the distal end of the second proximal mandrel 530. The distal portion 532 forces the proximal end 122 of the inner lumen 120 away from the inner wall of the proximal end 112 of the outer lumen 110.

The first extension tube 160 is inserted over the proximal end 534 of the second proximal mandrel 530 and the second extension tube 162 is inserted over the proximal end 524 of the first proximal mandrel 520. The first and second proximal mandrels 520, 530 are inserted into a hub mold (not shown) with the distal end 161, 163 of each of the first and second extension tubes 160, 162, respectively, as well as the proximal end 112, 122 of each of the outer and inner lumens 110, 120, inserted into the hub mold. A polymer, such as PELLETHANE®, is injected into the hub mold according to well known injection molding methods, forming the hub 150 around the proximal ends 112, 122 of each of the outer and inner lumens 110, 120, the distal ends 522, 532 of the first and second proximal mandrels 520, 530, and the distal ends 161, 163 of the first and second extension tubes 160, 162. The hub mold is removed from around the hub 150 and the first and second proximal mandrels 520, 530 are removed from the proximal ends 161, 163 of each of the first and second extension tubes 160, 162. The proximal ends 161, 163 of each of the first and second extension tubes 160, 162 are each attached to their respective luers 166, 170 as is well known in the art.

Alternatively, to manufacture the hub configuration with the spacer 151 as shown in FIG. 3A, the spacer 151 is inserted into the proximal end 112 of the outer lumen 110 between the outer wall of the inner lumen 120 and the inner wall of the outer lumen 110. The second proximal mandrel 530 is inserted into the outer lumen 110 between the outer wall of the inner lumen 120 and the inner wall of the outer lumen 110, with the inner lumen 120 disposed between the second proximal mandrel 530 and the spacer 151, to force the inner lumen 120 against the spacer 151. The first proximal mandrel 520 is inserted into the proximal end 122 of the inner lumen 120 to maintain the interior shape of the inner lumen 120.

Figure 5A:
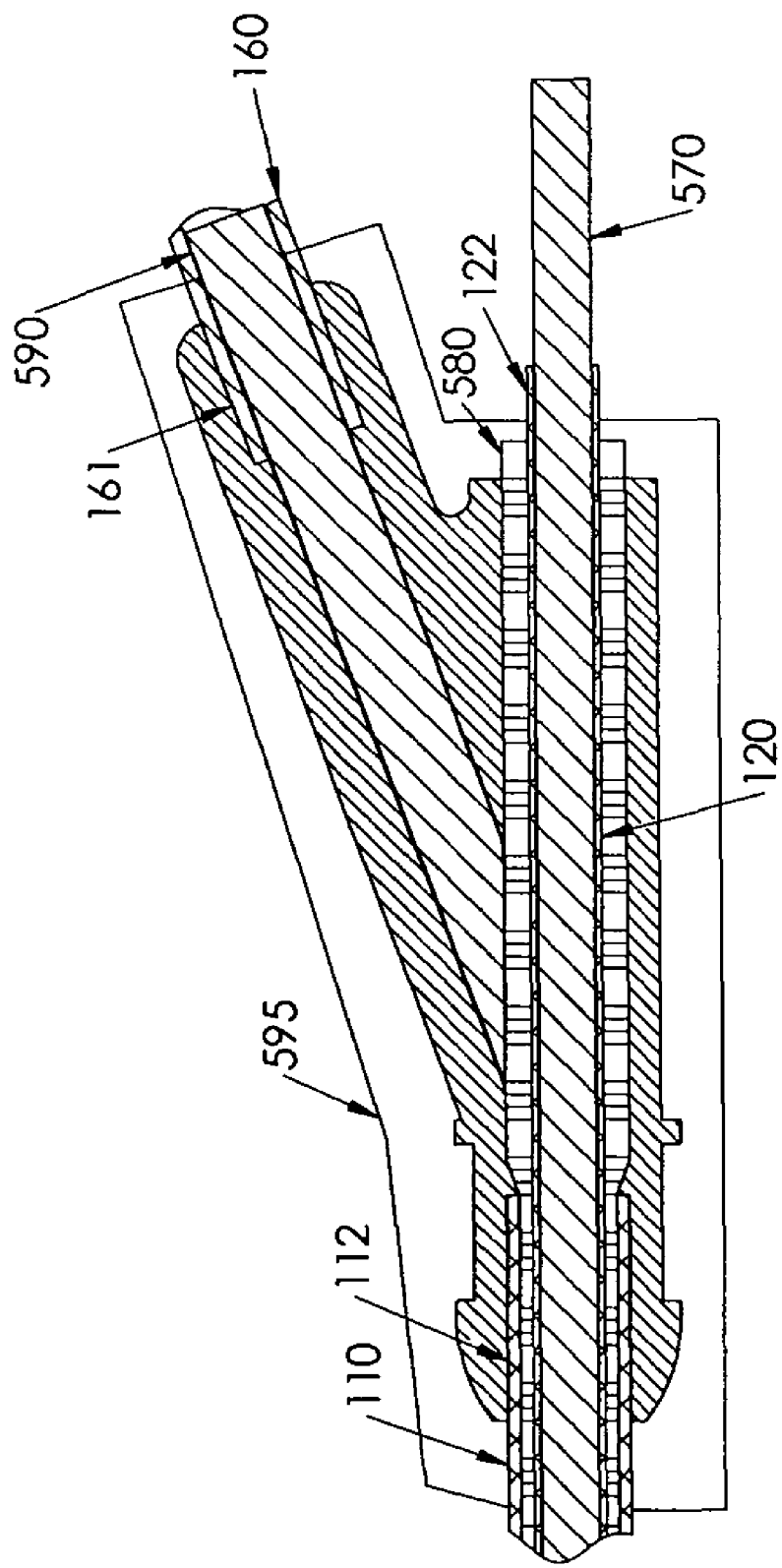
FIG. 5A is an enlarged sectional view showing insertion of mandrels used to manufacture the hub portion shown in FIGS. 3B and 3C.

To manufacture the hub 250 shown in FIG. 3B, referring to FIG. 5A, a first proximal mandrel 570 is inserted into the proximal end 122 of the inner lumen 120 to maintain the interior shape of the inner lumen 120. A spacer mandrel 580 having a generally annular cross section is disposed over the exterior of the distal end 122 of the inner lumen 110 and into the annular space between the outer lumen 110 and the inner lumen 120. A distal end of the spacer mandrel 580 tapers to a narrower diameter to fit inside the outer lumen 110 and to taper the passageway within the hub 250. The spacer mandrel 580 also includes a keyed portion that corresponds with the key 251b in the spacer 251 as shown in FIG. 3C. The proximal ends 112, 122 of the outer and inner lumens 110, 120, along with the mandrels 570, 580 are inserted into a first hub mold 595. A second proximal mandrel 590 is inserted into the first hub mold 595 to form the venous passageway 252. The first extension tube 160 is inserted over the second proximal mandrel 590 so that the distal end 161 of the first extension tube 160 is within the hub mold 595. Material to form the hub 250 is then injected into the first hub mold 595.

After the hub 250 cures, the spacer mandrel 580 is removed from the first hub mold 595 and the hub 250 is removed from the first hub mold 595. The spacer 251 is then inserted into the hub 250 over the proximal end 122 of the inner lumen 120 so that the key 251b is inserted into the space formed by the keyed portion of the spacer mandrel 580. The spacer 251 is inserted until the stepped portion 251c engages the hub 250. Optionally, an adhesive may be applied to the exterior of the spacer 251 prior to inserting the spacer 251 into the hub 250. The spacer 251 is secured to the proximal end 122 of the inner lumen 120 by applying a wicking adhesive into each through opening 255.

The hub 250 is then inserted into a second hub mold (not shown) to overmold the hub cap 256. The second extension tube 162 is slid over the first proximal mandrel 570 until the second extension tube 162 engages the stepped member 254. Material for the hub cap 256 is injected into the second mold to overmold the hub cap 256 of the proximal end of the hub 250, the spacer 251, and the distal end 163 of the second extension tube 162.

Figure 7:
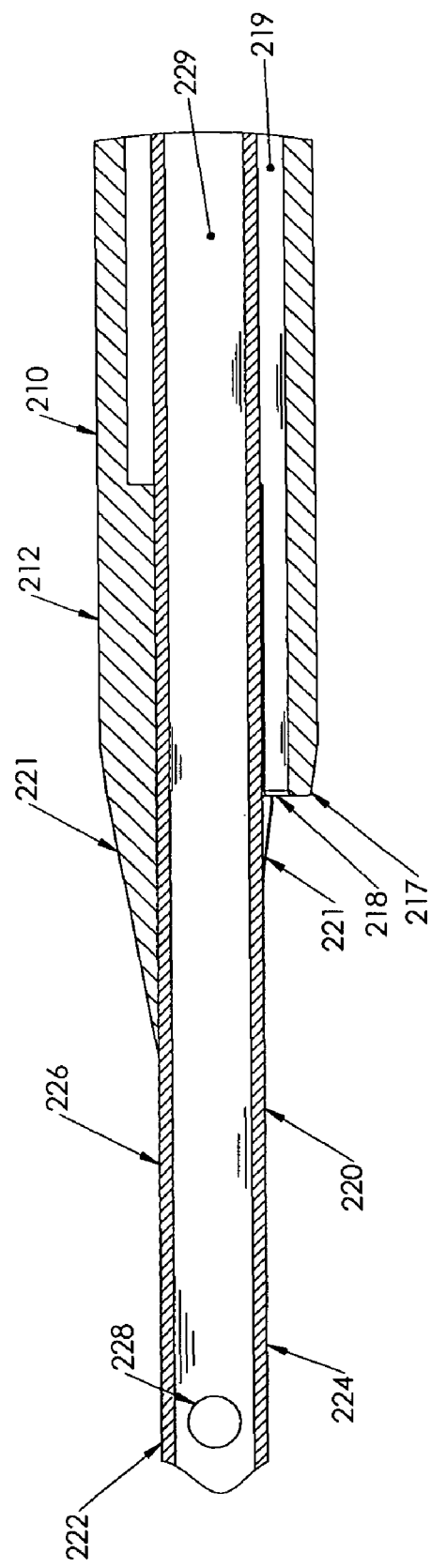
FIG. 7 is an enlarged side profile view, in section, of a distal end of the catheter assembly of FIG. 6.

A second embodiment of a catheter assembly 200 according to the present invention is shown in FIGS. 6, 6A, and 7. The catheter assembly 200 includes a proximal end 202 and a distal end 204. A longitudinal axis 206 extends through the catheter assembly 200 between the proximal end 202 and the distal end 204. The catheter assembly 200 is preferably constructed from CARBOTHANE® having a hardness of approximately 85A on the Shore Durometer scale, or one of the materials disclosed above with respect to the catheter assembly 100.

The design of the catheter assembly 200 is similar to the catheter assembly 100 described above, with the exception that the distal end 204 of the catheter assembly 200 differs from the distal end 104 of the catheter assembly 100. The proximal end 202 of the catheter assembly 200 is preferably the same as the proximal end 102 of the catheter assembly 100 as described above, so the proximal end 202 of the catheter assembly 200 will not be described. The alternative embodiments of the hubs 150, 250 described above and shown in FIGS. 3A and 3B may alternatively be used as well.

The catheter assembly 200 includes an outer lumen 210 having a distal end 212, a proximal end 214, and a body 216 extending therebetween. Preferably, the body 216 has an outer diameter of approximately 0.50 cm (0.20") and an inner diameter of approximately 0.42 cm (0.16"). The distal end 212 is preferably devoid of any side openings and has a plurality of end openings 218 at a distal tip 217 of the outer lumen 210. Each of the plurality of end openings 218 is separated from an adjacent end opening 218 by a rib 221. Preferably, three ribs 221 are present, although those skilled in the art will recognize that more or less than three ribs 221 may be used.

An inner lumen 220 is disposed within the outer lumen 210 to form a passageway 219 (FIG. 7) having an annular cross section between the inner lumen 220 and the outer lumen 210. The inner lumen 220 includes a distal end 222, a proximal end 224, and a body 226 extending therebetween. The body 226 has an outer diameter of approximately 0.30 cm (0.12") and an inner diameter of approximately 0.25 cm (0.10"). The inner lumen 220 has a plurality of side openings 228 helically spaced along the body 226 proximate to the distal end 222 of the inner lumen 220. Preferably, approximately five side openings 228 are present, although more or less than five side openings 228 may be used. Preferably, also, each side opening 228 has a diameter of approximately 0.13 cm (0.05"). A second passageway 229 is formed in the inner lumen 220, and serves to return the fluid that was drawn from the patient's body by the first passageway 219 and/or add additional fluids, such as medicaments, into the patient. The second passageway 229 terminates distally in a distal tip opening 230.

The ribs 221 space the inner lumen 220 away from the outer lumen 210 such that the inner lumen 220 is generally concentrically disposed within the outer lumen 210 at the distal end 204 of the catheter assembly 200. Each rib 221 is tapered from a greater to a lesser thickness from the proximal to the distal directions, as well as from a greater to a lesser height from the proximal to the distal directions.

Figure 8:
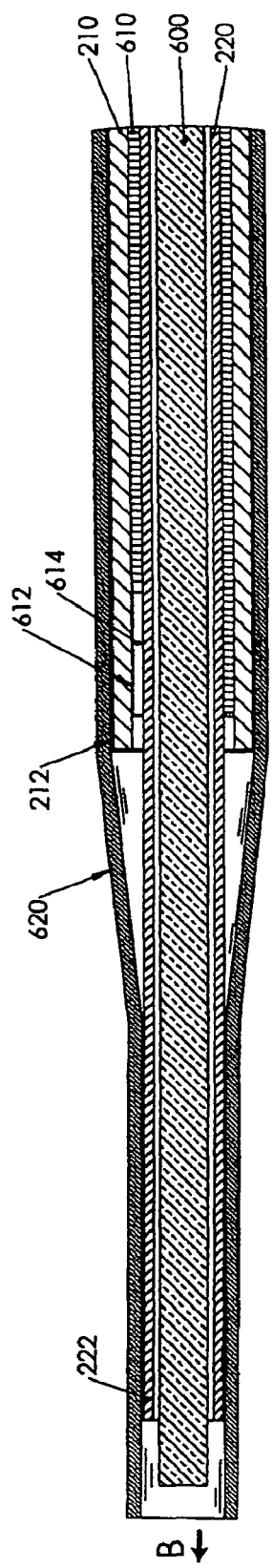
FIG. 8 is a sectional view showing the manufacturing of the distal end of the catheter assembly of FIG. 6.
Figure 8A:
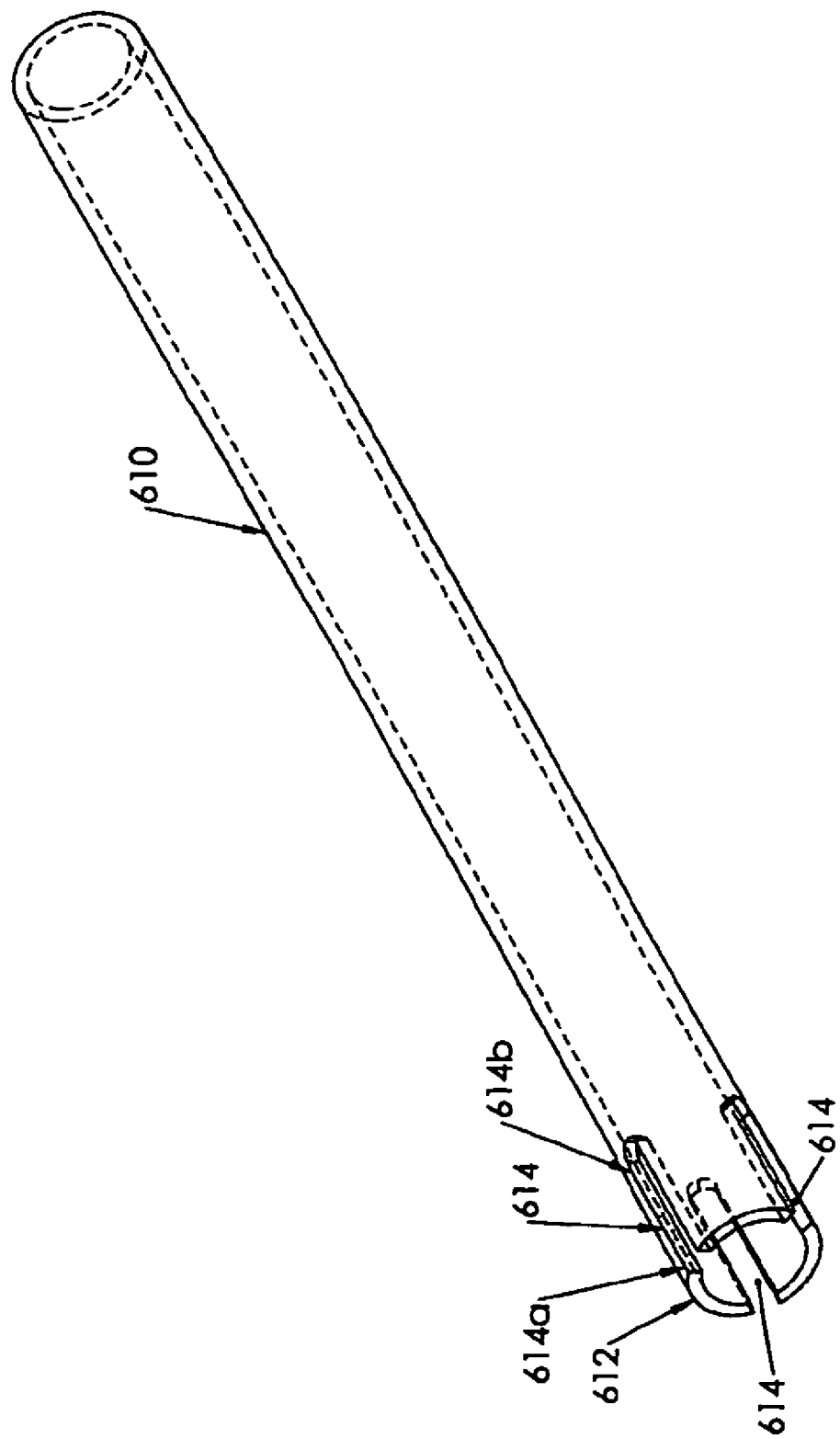
FIG. 8A is a perspective view of a mandrel used to fabricate the catheter assembly of FIG. 6.

To manufacture the catheter assembly 200, the inner lumen 220 is disposed over a first mandrel 600 as seen in FIG. 8. The first mandrel 600 is an elongated, preferably solid circular cylinder with an outer diameter slightly less than the inner diameter of the inner lumen 220 so that the inner lumen 220 is easily slid over the first distal mandrel 600. A second mandrel 610 is partially disposed over the inner lumen 220 such that the distal end 222 of the inner lumen 220 extends distally beyond the second mandrel 610. The second mandrel 610 includes a distal end 612 that includes a plurality of spaced cutouts 614. A perspective view of the second mandrel 610 is shown in FIG. 8A. The cutouts 614 are tapered so that the cutouts 614 span a larger arc at the most distal end 614a than at the more proximal end 614b. This taper allows the second mandrel 610 to be removed from the lumens 210, 220 by sliding the second mandrel 610 proximally with respect to the lumens 210, 220 after forming the distal end 204 of the catheter assembly 200.

Referring back to FIG. 8, the outer lumen 210 is disposed over the second mandrel 610 such that the distal end 212 of the outer lumen 210 extends slightly distally of the second mandrel 610, but not as far distally as the distal end 222 of the inner lumen 220. The lumens 210, 220 and the mandrels 600, 610 are slid longitudinally into a tapered third mandrel 620 as shown by the arrow B in FIG. 8. Heat is applied and the distal end 212 of the outer lumen 210 deforms and is forced into the spaced cutouts 614 in the second mandrel 610, forming the ribs 221. Preferably, the heat is applied by RF ultrasonic heating, although those skilled in the art will recognize that other heating methods may be used.

The proximal end 202 of the catheter assembly 200 is manufactured in the same manner as the proximal end 102 of the catheter assembly 100 as described above. The proximal end 202 of the catheter assembly 200 may be manufactured as shown in FIG. 3, without the spacer 151, or as shown in either of FIG. 3A or FIG. 3B, with either of the spacers 151, 251, as described above with respect to the catheter assembly 100.

Figure 9:
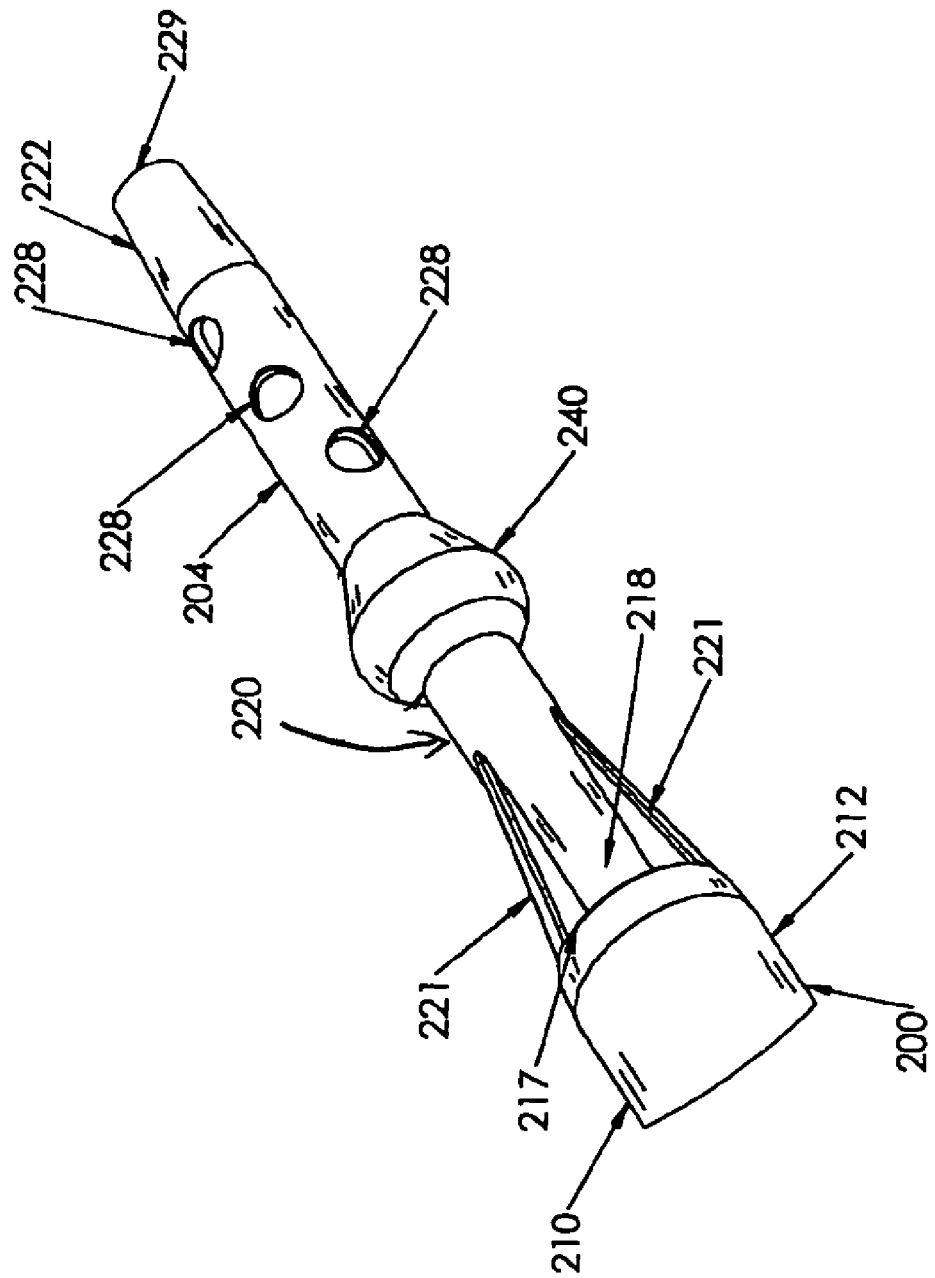
FIG. 9 is a perspective view of an optional distal end of the catheter assembly shown in FIGS. 6 and 7.

Optionally, the catheter assembly 200 may further include a bulbous portion 240, as shown in FIG. 9. The bulbous portion 240 is disposed on the inner lumen 220 between the ribs 221 and the side openings 228. The bulbous portion 240 extends distally of the ribs 221 to provide sufficient fluid flow into the end openings 218, centering the distal end of the inner lumen within the vessel so as not to restrict fluid intake into the outer lumen 210.

The bulbous portion 240 preferably has an outer diameter of approximately 0.50 cm (0.20"), or the same diameter as the outer diameter of the outer lumen 210. The bulbous portion 240 tapers in a proximal to a distal direction from the larger outer diameter of approximately 0.50 cm to the portion of the inner lumen 220 that is distal of the ribs 221.

Figure 10:
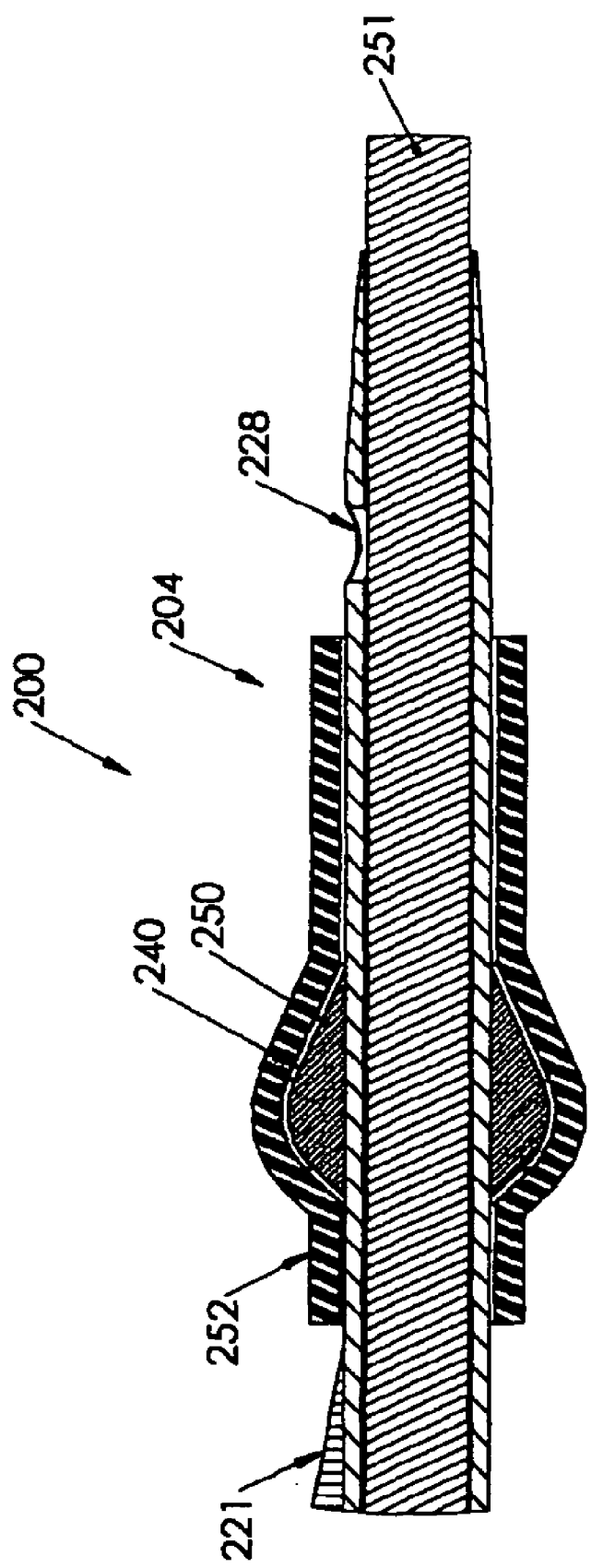
FIG. 10 is a side elevation view, in section, of a bulbous tip mold being applied over the distal end of the catheter assembly of FIG. 6.

To manufacture the catheter assembly 200 with the bulbous portion 240, the catheter assembly 200 is manufactured as described above. Referring now to FIG. 10, an overmold 250 is formed over the distal end 204 of the catheter assembly 200 to a location between the ribs 221 and the side openings 228 where the bulbous portion 240 is desired. To form the overmold 250, a mandrel 251 is inserted into the distal end 204 of the catheter assembly 200 to support the distal end 204. The distal end 204 of the catheter assembly 200 is then inserted into a mold 252, and bulb material is then injected into the mold 252, forming the overmold 250 within the mold 252 in the shape of the bulbous portion 240. The overmold 250 and the distal end 204 are heated to bond the bulbous portion 240 to the distal end 204 of the catheter assembly 200. Optionally, a secondary forming process, such as RF induction heating, may be performed on the bulbous portion 240 to smooth the transition between the bulbous portion 240 and the exterior of the distal end 204.

Figure 11:
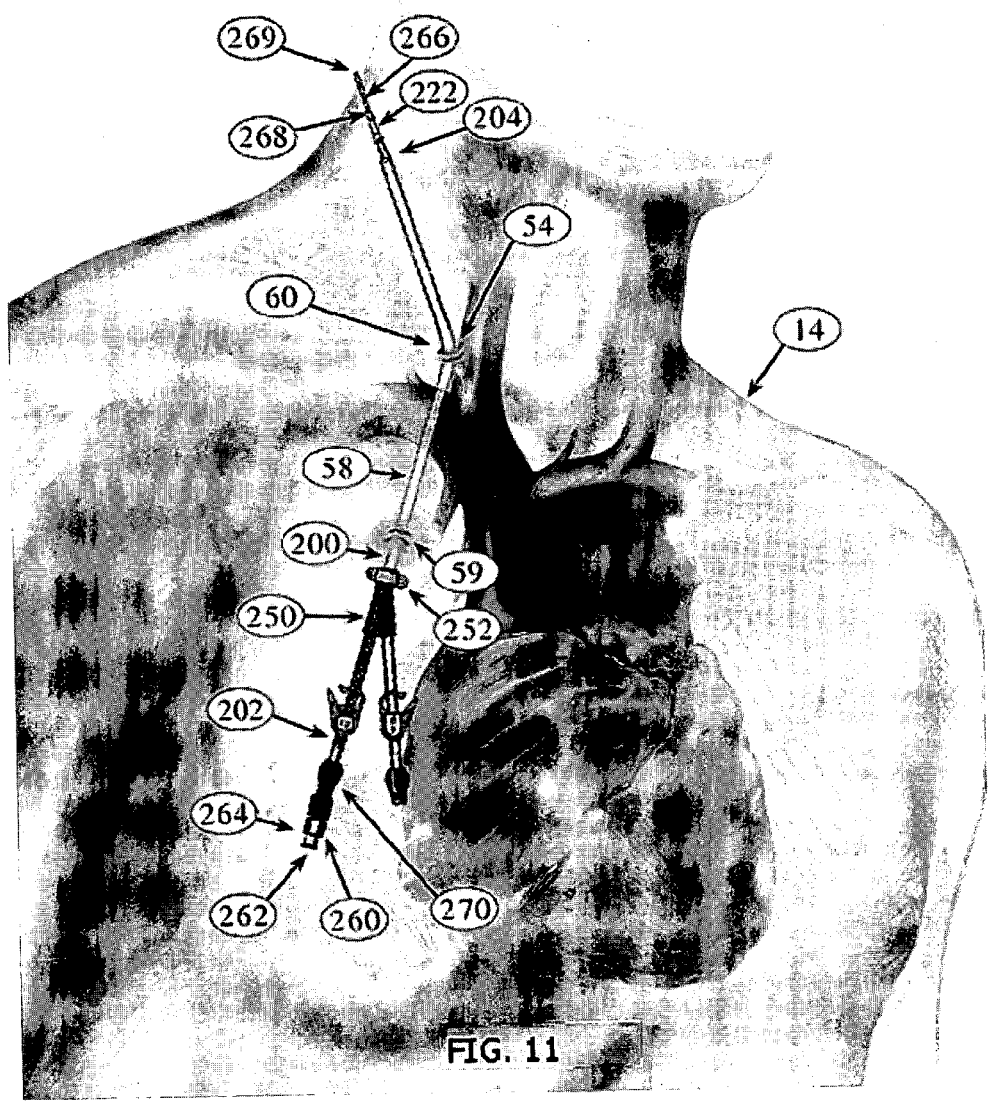
FIG. 11 is a partially broken away view of the catheter assembly of FIG. 9 subcutaneously tunneled in a body.

The catheter assembly 200 with the bulbous portion 240 is preferably inserted into the patient as follows. The bulbous portion 240 allows for insertion of the catheter assembly 200 without the need for an introducer sheath and/or a dilator, which are commonly used to expand an opening in a blood vessel to accommodate insertion of the catheter into the vessel. However, a stylet 260 is inserted through the inner lumen 220 as shown in FIG. 11. The stylet 260 stiffens the catheter assembly 200 to facilitate catheter insertion into the patient. The stylet 260 includes a proximal portion 262 that includes a swivel lock connector 264. The swivel lock connector 264 is configured to threadably connect to male threads of a luer connector 270 on the proximal end 202 of the inner lumen 220. The stylet 260 also includes a distal portion 266 that includes an elongated tubular body 268. The tubular body 268 extends through the inner lumen 220 and extends distally from the distal end 222 of the inner lumen 220. The stylet 260 also includes an elongated opening 269 that extends through the tubular body 268, as well as to and through the swivel lock connector 264. The opening 2269 has a diameter that is sized to allow a guide wire to extend therethrough during catheter insertion, as will be explained in more detail later herein.

Referring to FIG. 11, to insert the catheter assembly 200 into the patient, the portion of the catheter assembly 200 located just distally of the hub 250 may be located within a subcutaneous tunnel 58 in the patient's body 14, using various well-known tunnelling techniques. In one technique, the distal end 204 of the catheter assembly 200 is pulled through the tunnel 58 from the lower end 59 of the tunnel 58, while forming the tunnel 58 using a trocar or other tunnelling tool, leaving the hub 250 outside of the tunnel 58 and the distal end 204 extending outwardly from an upper end 60 of the tunnel 58 near the area to be catheterized 54. One technique for tunnelling the catheter assembly 200 through a subcutaneous area is disclosed in U.S. Patent Publication No. US 2005/0,080,398, which is owned by the assignee of the present invention and is incorporated by reference herein as though fully set forth.

Figure 12:
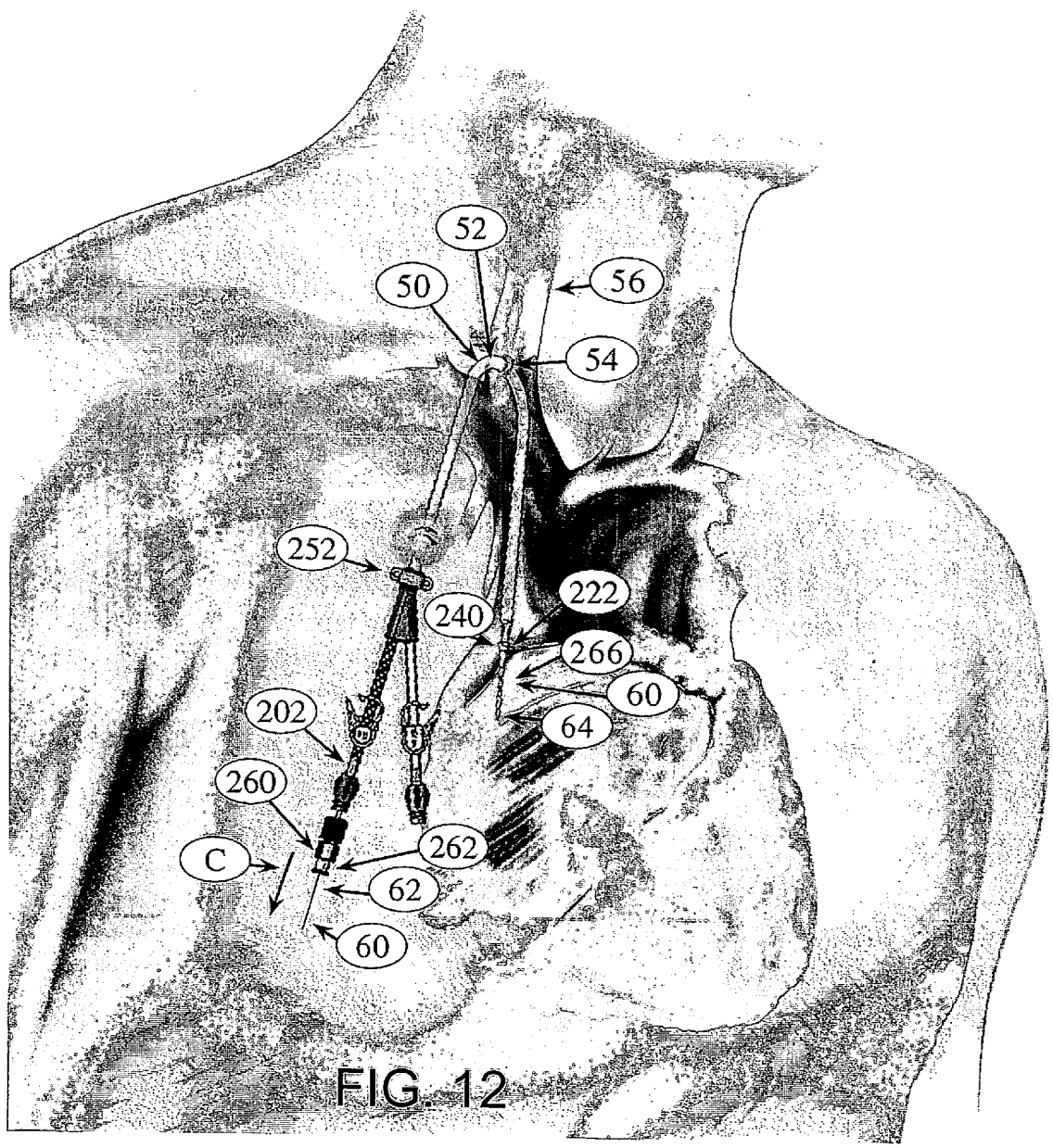
FIG. 12 is partially broken away view of the catheter assembly of FIG. 11, having been inserted into an area to be catheterized.

Next, an incision 50, shown in FIG. 12, is made at the insertion site 52, either before or after tunneling. The underlying vessel is then identified by aspiration with a syringe or other introducer apparatus, such as the RAULERSON ONE-STEP introducer, near or proximate the area to be catheterized 54. If the catheter assembly 200 is used for hemodialysis and the area to be catheterized 54 is the internal jugular vessel 56, the incision 50 is made in the clavicular triangle region, as shown for example, in FIG. 12. The exact location of the incision 50 can be varied by the physician. In accordance with the Seldinger technique, a narrow needle is inserted through the incision 50 and into the vessel 56, and the vessel 56 is cannulated. A guide wire 60 is then passed through the needle, or other introducer into the cannulated vessel, and the needle is removed. A proximal end 62 of the guide wire 60 extends exterior of the patient, with a distal end 64 of the guide wire extending into the vessel 56.

Next, the proximal end 62 of the guide wire 60 is inserted into the opening through the distal portion 266 of the stylet 260 and through the stylet 260 until the proximal end 62 of the guide wire 60 exits the proximal portion 262 of the stylet 260. The catheter assembly 200 is advanced distally along the guide wire 60 until the distal end 222 engages the incision 50 made at the insertion site 52. The distal end 222 is advanced through the incision 50 and into the vessel 56 that is being catheterized by advancing the catheter assembly 200 in a distal direction while oscillating the bulbous portion 240 in a circular motion. The oscillating motion stretches the incision 50 as well as the wall of the vessel 56 where the guide wire 60 penetrates the vessel 56.

As the distal end 222 is advanced into the vessel 56, the bulbous portion 240 further stretches the incision 50 and the wall of the vessel 56 so that the distal end 222 may be further advanced into the vessel 56. As the bulbous portion 240 advances into the vessel 56, the wall of the vessel 56 contracts around the inner lumen 220, proximal of the bulbous portion 240, minimizing blood loss from the vessel 56.

The catheter assembly 200 is further advanced into the vessel 56, and the ribs 221 engage the wall of the vessel 56. Since the vessel 56 had just been stretched by the bulbous portion 240, the wall of the vessel 56 easily expands to accommodate the increasing size of the ribs 221 as the ribs 221 are advanced into the vessel 56. The ribs 221 expand the wall of the vessel 56 to accommodate the outer diameter of the outer lumen 210, which is preferably the same size as the outer diameter of the bulbous portion 240, which had just stretched the wall of the vessel 56.

After the catheter assembly 200 is inserted a desired distance into the patient, the guide wire 60 is removed from the proximal end 202 of the catheter assembly 200 and the stylet 260 by pulling the proximal end 62 of the guide wire 60 proximally and out of the stylet 260 in the direction of the arrow "C". The stylet 266 is then removed from the catheter assembly 200 by unthreading the swivel lock 264 from the luer connector 270 and pulling the stylet 260 proximally from the catheter assembly 200, also in the direction of the arrow "C".

Next, the incision 50 is closed and the proximal end 202 of the catheter assembly 200 is secured to an external surface of the body 14 such as by suturing the suture wing 252 on the hub 250 to the body 14. Alternatively, the incision 50 may be closed after securement.

The proximal end 202 of the catheter assembly 200 is connected in fluid communication to a hemodialysis unit, or other fluid transfer equipment (not shown), according to procedures well known in the art, and dialysis may now begin.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A co-axial catheter assembly comprising:
   a) a first catheter lumen extending along an axis, wherein the first catheter lumen has an open first distal end and a first proximal end;
   b) a second catheter lumen extending along the axis, wherein the second lumen is disposed generally within the first catheter lumen, and wherein the second lumen includes a second distal end and a second proximal end;
   c) a hub disposed at the first proximal end of the first catheter lumen and defining at least first and second passages extending therethrough, the second passage axially aligned with the first catheter lumen and the second catheter lumen, with the second proximal end of the second catheter lumen extending partially along the second passage proximally of the first proximal end of the first catheter lumen; and
   d) a hub spacer sized and configured to be simultaneously insertable into a hub proximal end and over and along the second proximal end of the second catheter lumen that centers the second proximal end with respect to the first proximal end of the first catheter lumen,
   wherein the first passage and second passage join within the hub to a distal catheter-receiving passageway of the hub, the hub spacer includes a distal end that is tapered to block access to the second passage from distally thereof about the second catheter lumen and to direct fluid flow through the first passage from a first extension tube, and wherein the hub spacer includes a key cooperable with a keyway of the hub for angularly orienting the hub spacer with respect to the hub.

2. The co-axial catheter assembly according to claim 1, wherein a tubular portion of the second catheter lumen extends distally of the first distal end, and the at least one distal end spacer is tapered in a distal direction from the first distal end partially toward the second distal end.

3. The co-axial catheter assembly according to claim 1, wherein a distal end spacer extends proximally into and occluding a passageway of the first catheter lumen and around the second catheter lumen at the distal tip of the first catheter lumen, and a tubular distal end portion of the second lumen extends distally of the first distal end and the distal end spacer.

4. The co-axial catheter assembly according to claim 1, wherein the hub spacer includes a stop cooperable with portions of the hub to stop farther distal movement of the hub spacer at full insertion depth during axial movement of the hub spacer along the second passage.

5. The co-axial catheter assembly according to claim 1, wherein the hub spacer includes small openings for wicking of adhesive liquid to bond and seal the hub spacer to the hub and the second proximal end.

6. The co-axial catheter assembly according to claim 1, wherein a cap is fixedly connected to the hub and the hub spacer securing the hub spacer in the hub.

7. A co-axial catheter assembly according to claim 1, wherein the distal end spacer is formed from a piece initially separate from the first catheter lumen and the second catheter lumen and is sized and configured to be simultaneously joined to both the first and second catheter lumens, and at least one portion of which is disposed between the first catheter lumen and the second catheter lumen at the distal end of the first catheter lumen.

8. The co-axial catheter assembly according to claim 1, wherein the hub further comprises a hub connector fixedly connected to the hub at a proximal end of the second passage, wherein the hub connector fixedly retains the spacer within the hub.

9. A co-axial catheter assembly comprising:
a) a first catheter lumen extending along an axis, wherein the first catheter lumen has an open first distal end and a first proximal end;
b) a second catheter lumen extending along the axis, wherein the second lumen is disposed generally within the first catheter lumen;
c) a hub disposed at the first proximal end of the first catheter lumen and defining at least first and second passages extending therethrough, the second passage axially aligned with the first catheter lumen and the second catheter lumen, with the second proximal end of the second catheter lumen extending partially therealong proximally of the first proximal end; and
d) a hub spacer adapted to be insertable into a hub proximal end in a pre-selected angular orientation and simultaneously over and along the second proximal end of the second catheter lumen that centers the second proximal end with respect to the first proximal end of the first catheter lumen,
wherein the first passage and second passage join within the hub to a distal catheter-receiving passageway of the hub, the hub spacer includes a distal end that is tapered to block access to the second passage from distally thereof about the second catheter lumen and to direct fluid flow through the first passage from a first extension tube, and
the hub spacer includes a key cooperable with a keyway of the hub for angularly orienting the hub spacer with respect to the hub to be in said pre-selected angular orientation.

10. The co-axial catheter assembly according to claim 7, wherein the first distal end comprises at least one distal opening disposed proximally of the spacer.

11. The co-axial catheter assembly according to claim 7, wherein the at least one spacer extends distally of the first distal end.

* * * * *